United States Patent [19]
Saccomanno, III

[11] Patent Number: 6,109,150
[45] Date of Patent: Aug. 29, 2000

[54] TORQUE INDICATING WRENCH

[76] Inventor: Matthew Saccomanno, III, 1414 Rideway St., Oceanside, Calif. 92054

[21] Appl. No.: 09/369,963

[22] Filed: Aug. 6, 1999

[51] Int. Cl.[7] .................................................. B25B 23/142
[52] U.S. Cl. .............................................. 81/478; 81/479
[58] Field of Search .............................. 81/467, 478, 479, 81/483; 73/862.21, 862.22, 862.23

[56] References Cited

U.S. PATENT DOCUMENTS

| | | | |
|---|---|---|---|
| 2,715,333 | 8/1955 | Larson | 73/139 |
| 2,934,946 | 5/1960 | Engquist | 73/139 |
| 3,747,423 | 7/1973 | Mitchell | 73/139 |
| 3,895,517 | 7/1975 | Otto | 73/88.5 R |
| 4,958,541 | 9/1990 | Annis et al. | 81/479 |
| 5,337,638 | 8/1994 | Coss et al. | 81/438 |
| 5,368,480 | 11/1994 | Balfour et al. | 433/141 |
| 5,557,994 | 9/1996 | Nakayama | 81/478 |
| 5,597,113 | 1/1997 | Ray, Sr. | 433/141 |
| 5,734,113 | 3/1998 | Vogt et al. | 73/862.23 |

*Primary Examiner*—Timothy V. Eley
*Assistant Examiner*—Dung Van Nguyen
*Attorney, Agent, or Firm*—Charles F. Reidelbach, Jr.; Presseisen & Reidelbach, P.C.

[57] ABSTRACT

A torque applying and indicating wrench is comprised of a pawl with a torque sensing end for both ratcheting, and direct sensing of torque during application. The torque sensing end is bifurcated into a cantilevered flexing beam and an optional reference beam. The flexing beam engages one or more ratchet teeth from a ratchet wheel contained in the wrench head of an elongated tool body. Torque is then transduced and indicated either mechanically or electronically.

20 Claims, 7 Drawing Sheets

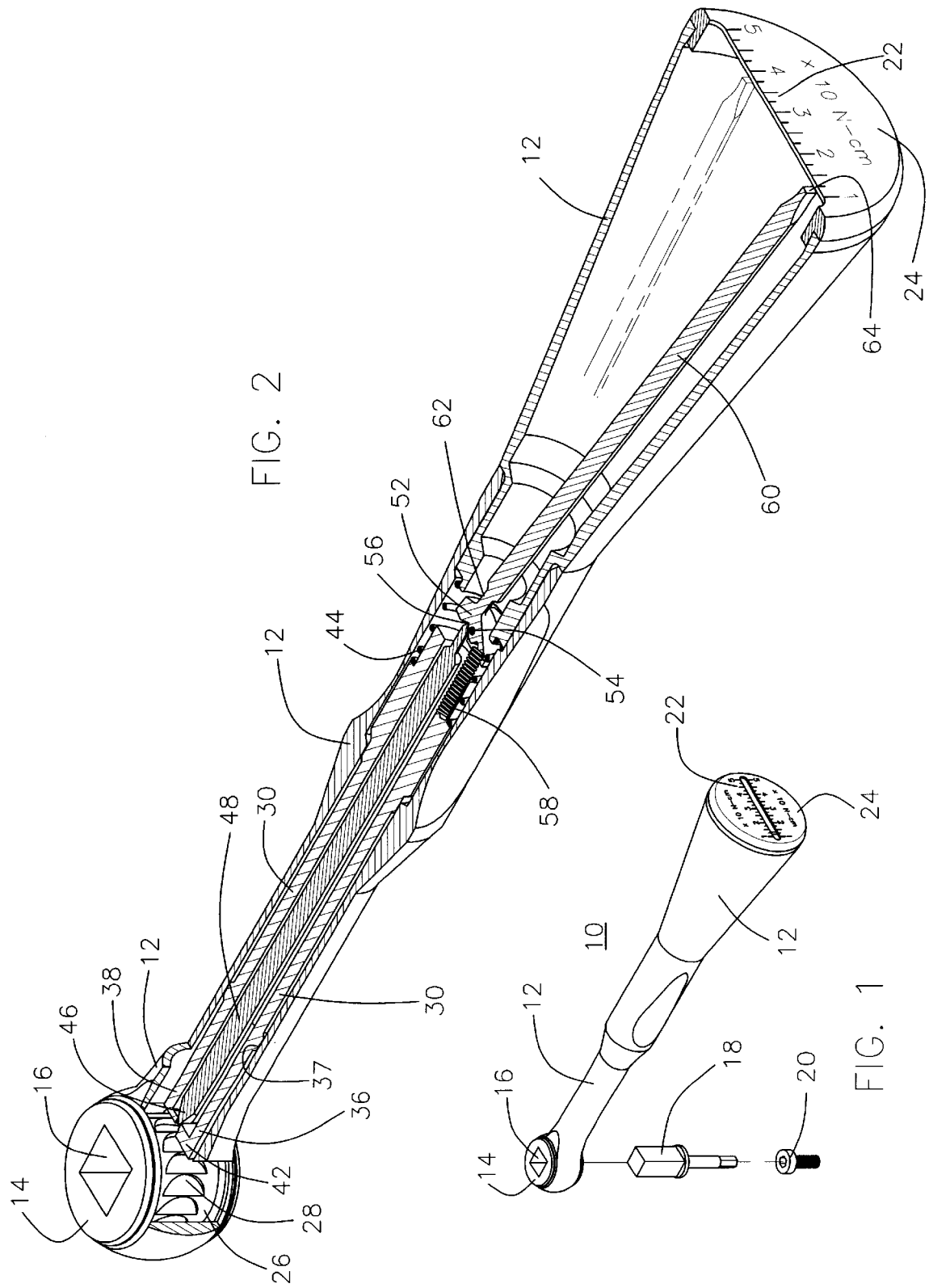

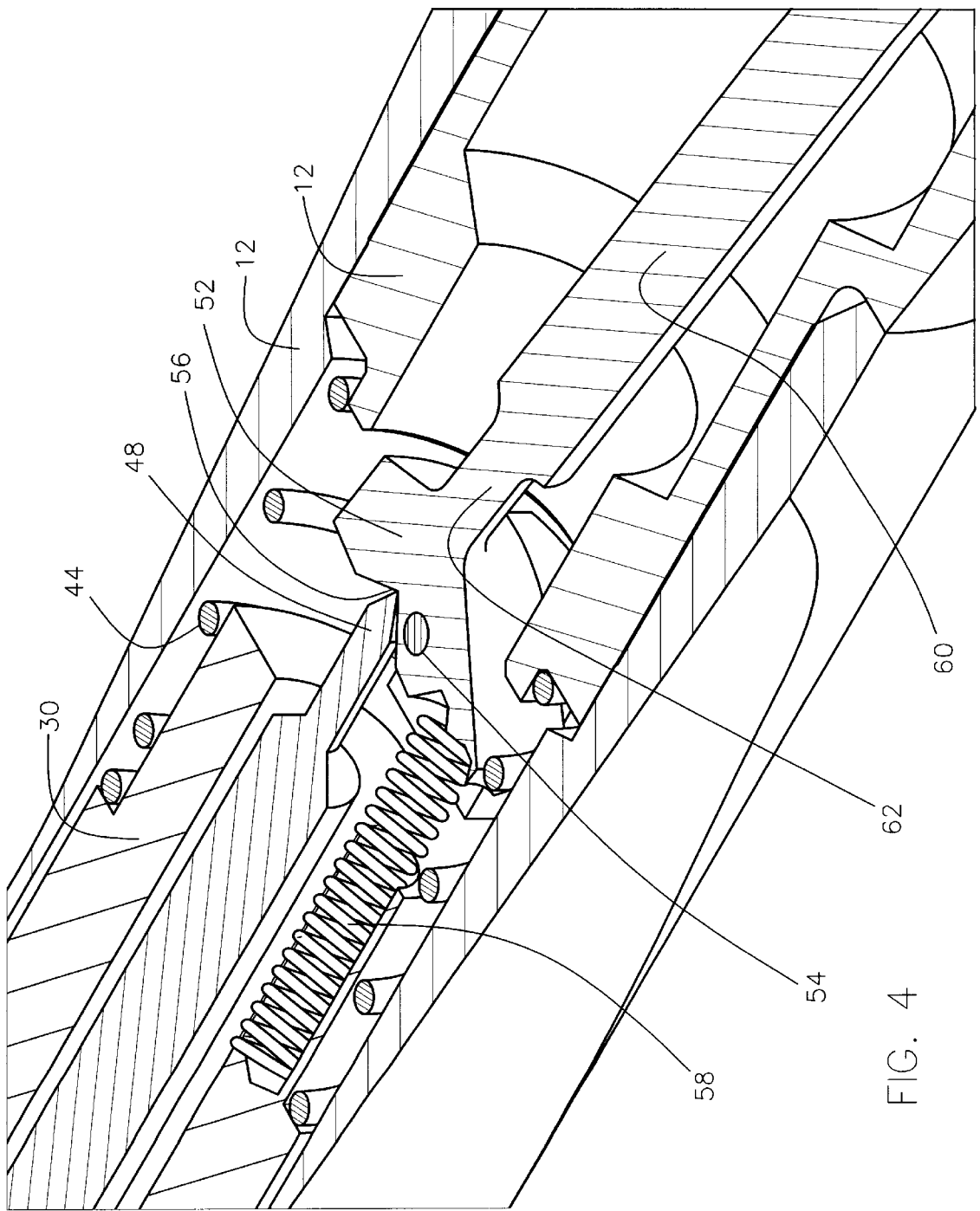

TORQUE INDICATING WRENCH

FIELD OF THE INVENTION

The present invention relates generally to tools for restorative prosthodontia and more particularly to a torque indicating tool for driving and tightening components used in the replacement of missing teeth. This invention may have applications in orthopedic or neurological surgical procedures where screws, bolts, and brackets are used to mend fractured hips, vertebrae, and other bones. This torque indicating tool may also have non-medical applications where a compact and contaminant tolerant tool design is required.

BACKGROUND OF THE INVENTION

Prosthodontic restorative systems, tools and techniques are well-known in the prior art. For patients missing some or all of their teeth, a dental implant fixture is implanted in a bore made in a patient's jawbone after the gum tissue has been pealed back. The fixture typically includes an internally-threaded socket which receives one or more components used for attaching a permanent dental restoration, such as a tooth.

The various components of prosthodontic restoration are typically driven and tightened with respect to the implant combination or each other using many different drivers or wrenches, one for each type of restorative component. The prosthodontist or surgeon manipulates the drivers manually or through the use of an automatic device. Automatic devices usually include a torque control mechanism to insure that components are tightened to their optimum torque.

Precise and complete tightening of the components in a restoration is often difficult to achieve manually. The surgeon must take care to apply sufficient and consistent torque to these fixtures, screws or bolts, otherwise over-torque can lead to needless pain and rehabilitation, while under-torque leads to loosened components and support resulting in displaced fractures. Components that loosen and back-out of their fittings, require repeated office visits and even additional surgery for retightening. While automatic devices generally overcome this problem, such devices are costly and somewhat cumbersome to use. Moreover, the accuracy of such devices will degrade over time by wear, tear and adverse effects of sterilization.

Small, easy to use tools that ratchet and indicate torque applied to a given workpiece would be useful in the aforementioned fields. Various ratchet wrenches have been invented, and are usually grouped into two types: torsional ratchet wrenches such as the "Dental Implant Wrench," U.S. Pat. No. 5,368,480 issued to Balfour et al., and ratchet pawl wrenches such as the "Ratchet Handle with Torque Adjustment," U.S. Pat. No. 5,557,994 issued to Nakayama.

Other art, such as with the "Torque Control Ratchet Wrench," U.S. Pat. No. 5,337,638 issued to Coss et al., simply teaches a handle breaking out of alignment with a cam member when a torque limit is reached. This feature creates a requirement for a large set of such tools, because a single tool does not cover more than one torque value.

Earlier art, such as with "Improvements In or Relating to Torque-Indicating Wrenches," U.K. Patent No. 825,282 to Prosser, teaches a semi-circular rotating pawl with two notches as a way to engage a ratchet wheel. A termination member develops the torque which is then transmitted through a torque-transmitting lever to a torque-reaction spring.

In the instant invention, the concept of using a flexible beam extending from a pawl to both ratchet and sense torque encountered during engagement and rotation of a workpiece is believed to be novel.

There is therefore a need to provide a new tool for driving components used in a dental prosthodontic restoration and orthopedic reconstruction that overcomes the problems of torque application and the other issues of the related art.

It is an object of the present invention to provide a single tool for manually driving components of a dental restoration system that precisely and reproducibly tightens components to a specified, measurable torque in a simple and cost effective way.

It is another object of the present invention to provide for an indication of graduated torque values during the application and measurement of torque.

It is still another object to provide a tool for driving components in a dental restoration system that can be used with a variety of different makes and styles of component parts.

It is yet another object of the present invention to provide a means for both ratcheting and sensing of actual torque during insertion of implant devices, along with the parallel diagnostic value of such torque measurement.

It is yet another object of the present invention to provide a robust tool with the ability to withstand large torque overloads without damage to the tool, or its ability to transduce and indicate torque.

It is still yet another object of the present invention to provide for an inexpensive torque indicating tool that is simple, readily cleanable, user-friendly, requires minimal maintenance and calibration, and that can be driven manually (such as by ratchet) or automatically (such as by a powered handpiece).

It is still yet another object of this invention to provide this torque indicating tool in a handheld, easy to use wrench format, that is functionally tolerant of biological fluids, capable of withstanding chemical and steam sterilization processes and yet retain precision in measuring torque.

The aforementioned background has outlined some of the more pertinent objects of the present invention. These objects should be construed to be merely illustrative of some of the more prominent features and applications of the invention. Many other beneficial results can be attained by applying the disclosed invention in a different manner or modifying the invention as will be described. Accordingly, other objects and a fuller understanding of the invention may be had by referring to the following illustrations, and the written disclosure of the Detailed Description of the Invention.

SUMMARY OF THE INVENTION

These and other objects of the invention are provided in a torque indicating tool for driving and tightening components used in a dental prosthodontic restoration, a process that currently uses many interchangeable wrenches or drivers, and many torque elements each having predetermined torque ratings. In the preferred embodiment, the tool includes an annular wrench head, tool interface, and an essential ratchet wheel with circumferential teeth or engagement means. This wrench head is located at the terminal end of a tool body, which is then used to engage and secure the workpiece implant fixture into the jawbone of a patient, at a required torque value. The torque that is applied must be transduced and indicated for display by the tool, if the prosthodontist is to apply the proper amount of torque to the various workpieces.

The transduction of torque into mechanical movement uses a novel pawl to both ratchet and sense the torque. Specifically, this tool is comprised of a pawl with a sensing end that is engaged and deflected by at least one of the ratchet teeth or equivalent, during torque application. Specifically, the sensing end may be bifurcated, and is commonly embodied by a cantilevered flexing beam, adjacent to an optional reference beam that itself is integral to the pawl or the tool body. The flexing beam engages at least one of the ratchet teeth, and is proportionally deflected by the applied torque. The deflection of the flexing beam causes a gap located between the flexing beam and the reference beam to enlarge proportionately, which causes a wedge at the end of a slidable rod to be automatically inserted therein. The wedge reversibly adjusts its slidable position according to the size of the gap, which in turn drives the movement of the slidable rod.

The torque-indicating mechanism takes the reversible, slidable movement of the rod and converts it into nutational movement of a pivot head that is under positive counter rotational bias. This is accomplished by use of a simple pivot and lever mechanism, where the rod bears upon the pivot head at a pivot bearing positioned adjacent to an axle that secures the pivot head to the tool body.

Attached or integral to the pivot head is a pointer that is deflected by the rotation of the pivot head about the axle. The tip of the pointer moves across a graduated torque scale at the butt-end of the tool body, where it can be visualized by the user.

Alternatively, both mechanical transduction and mechanical indication of torque can be accomplished by generic sensing systems, such as by Hall effect sensors, proximity sensors, various strain gauge sensors, and LED/light detector systems, and other electronic means well known to those skilled in the art. Using such sensors may partially or completely eliminate the need for the mechanical transducing and indicating mechanisms. This may improve the precision and reliability of this tool by eliminating many of the moving parts.

The foregoing has outlined some of the more pertinent objects of the present invention. These objects should be construed to be merely illustrative of some of the more prominent features and applications of the invention. Many other beneficial results can be attained by applying the disclosed invention in a different manner of modifying the invention as will be described. Accordingly, other objects and a fuller understanding of the invention may be had by referring to the following Detailed Description of the Invention, which includes the preferred embodiment.

BRIEF DESCRIPTION OF THE DRAWINGS

FIG. 1 is a top perspective view of the present invention in one application.

FIG. 2 is a longitudinal cross-sectional view of the present invention.

FIG. 4 is a close-up mesial view of the indicating mechanism of the present invention.

DETAILED DESCRIPTION OF THE INVENTION

Figure 3:
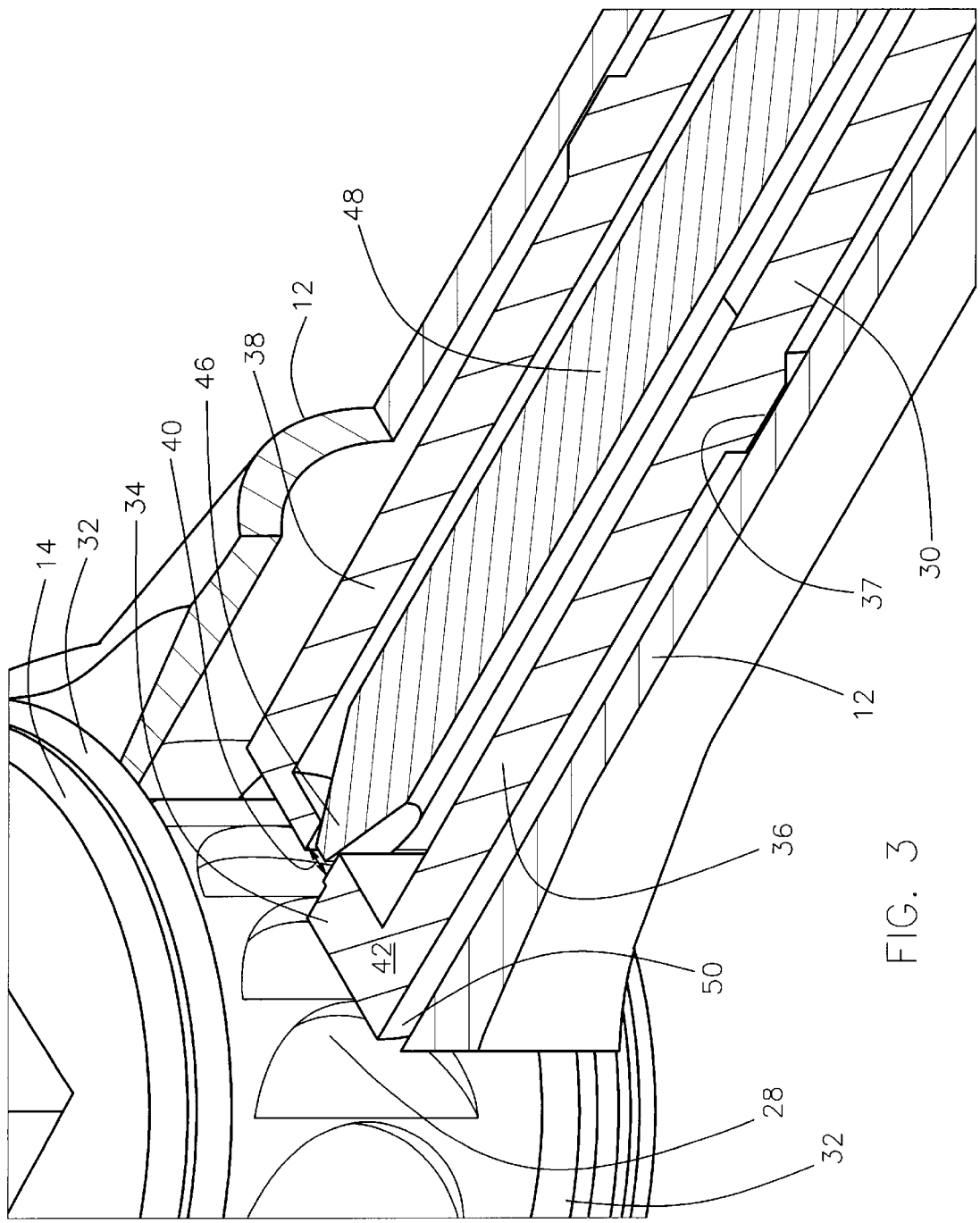
FIG. 3 is a close-up distal view of the transducing mechanism of the present invention.

In the following detailed description, certain specific terminology will be employed for the sake of clarity and a particular embodiment described in accordance with the requirements of 35 U.S.C. 112, but it is to be understood that the same is not intended to be limiting and should not be so construed inasmuch as the invention is capable of taking many forms and variations within the scope of the appended claims.

Referring to FIG. 1, a torque wrench 10 is shown, with most elements and components encased in a tool body 12. The distal end of the tool body 12 includes an annular wrench head 14 having a tool interface 16 for coupling to workpieces such as tool bit 18 which mates with a screw 20. A graduated scale 22 of torque values appears on the butt-end 24 of the tool body 12.

As shown in FIG. 2, the wrench head 14 has a ratchet wheel 26 having multiple ratchet teeth 28 circumferentially located thereon. While a sufficient number of ratchet teeth 28 may be used to encircle the entire ratchet wheel 26, this number is at least one tooth or engagement fixture, with a typical number being about twelve-to-forty ratchet teeth 28. Those who are skilled in the art will recognize that a friction clutch, or multiple ridges, knurls, or other means of physical engagement may be used in place of the ratchet teeth 28, their only requirement being the ability to engage with the pawl 30.

FIG. 2 illustrates the detailed mechanical elements for transducing torque into mechanical movement, and FG. 3 gives a close-up view of the same. The ratchet wheel 26 is coupled to the wrench head 14 through a bearing sleeve 32 located on each planar side of the wrench head 14. The bearing sleeves 32 allows the ratchet wheel 26 to freely rotate within the wrench head 14, relative to the pawl 30. The sensing end 42 of the pawl 30, both nested or fitted within the tool body 12, are urged toward the distal end of the wrench 10 toward the ratchet wheel 26 by a ratchet spring 44 (seen in FIG. 2). This spring 44 is preferably compressed, and it is this energy that urges the pawl 30 towards the ratchet wheel 26, and engages the ratchet teeth 28 or its well known equivalent. Alternatively, this ratchet spring 44 may be in a different location within the tool body 12, or be in a variety of forms. For example, hollow cylinders of deformable material may be used to give a similar spring-like effect in the urging of the pawl 30 towards the ratchet wheel 26. Other springable means well known to those skilled in the art may also be used.

As best illustrated in FIG. 3, the ratchet teeth 28 engage the protuberance 34 located on the distal end of a flexing beam 36. The protuberance 34 is designed and machined into the end of the flexing beam 36, which results in the flexing beam 36 being slightly longer than the adjacent and juxtaposed reference beam 38. This increased length allows the flexing beam 36 to solidly engage with the ratchet teeth 28, while the reference beam 38 is able to avoid direct contact with the ratchet wheel 26, and therefore remain stationary. This engagement stops the ratchet wheel 26 from freely rotating. The rotation of the ratchet wheel 26 is with and with respect to the tool body 12. This movement allows the connected wrench head 14 to engage and turn a workpiece (FIG. 1) unidirectionally.

FIG. 3 also shows pawl 30 with its distal end serving as the sensing end 42, which is bifurcated longitudinally into the aforementioned flexing beam 36 and the reference beam 38. Both of these beams 36, 38 are minimally separated by a gap 40 which increases as the distance between beams 36, 38 expands during torque application. Both of these beams 36, 38 are shown cantilevering from an annular fulcrum 37. This fulcrum 37 is critical for the proper displacement of the flexing beam 36, but is optional for the reference beam 38. It is well known to those skilled in the art, that the fulcrum 37 need not be annular, but may be partially annular or non-annular, as long as it is positioned as a proper fulcrum for the flexing beam 36.

Inserted between the flexing and reference beams 36, 38 is a wedge 46 or tapered end of rod 48. This wedge 46 can be coated with Teflon®, hardened steel, diamond or other gem or wear-resistant surfaces well known in the art, in order to improve the long-term toughness and reliability of the wedge surface. The slope of this wedge 46 may vary, which will effect the longitudinal distance that the rod 48 will slide adjacent to the pawl 30. This will effect the sensitivity of the transduction of torque into longitudinal movement of the rod 48. The slope may also vary at different points along the wedge 46, which may amplify or reduce the longitudinal movement of the rod 48 given an equal amount of torque. This will directly bear upon the calibration or sensitivity of torque indication at different ends of the graduated torque scale. In this manner, the graduated scale 22 may become a non-linear scale that would indicate torque over a larger working range.

The relative sequence of the mechanical motions of torque transduction at the distal end of this tool will be discussed below in reference to FIGS. 5–7.

FIG. 2 illustrates the detailed mechanical elements for indicating torque from mechanical movement, and FIG. 4 gives a close-up view of the pivot and lever mechanism.

A pivot head 52 is coupled to the proximal end of the pawl 30 by an axle 54, about which the pivot head 52 is able to make radial nutational or pivoting movement. The proximal end of the rod 48 interfaces to the pivot head 52 by a generic pivot bearing 56. As torque is applied by the torque wrench 10, a rotational bias means 58 connected between the pawl 30 and the pivot head 52, drives the nutational movement of the pivot head 52, as the rod 48 reversibly slides in the distal direction away from the pivot head 52. It is well known in the art, that the rotational bias means 58 may be a compressed pivot spring, or some other compressible or expanding driver that is well known to those skilled in the art.

As an alternative to a one-piece rod 48, the rod may be two-pieces interconnected by a compression spring encased in a sleeve. This will allow the rod to absorb intermittent shocks caused by sudden large applications of torque, mishandling or droppings to the floor, without damaging the tool mechanism and its ability to transduce and indicate torque.

To complete the mechanical indication of torque, the pivot head 52 has an attached pointer 60 projecting in a proximal direction away from the pivot head 52. As seen in FIG. 2, the torque-indicating rotation of the pivot head 52 about the axle 54, translates into a sweep by the pointer 60 transversing the proximal end of the tool body 12, referred to as the butt-end 24. Calibration adjustment of pointer 60 can be made by adjusting the angle of attachment that the pointer 60 has to the pivot head 52. This is usually done by manually bending the pointer 60 at the bend region 62 existing therebetween. The proximal end of the pointer may have a tapered pointer tip 64 (FIG. 2) to more precisely indicate the position of the pointer from the graduated scale 22 (FIG. 2).

The relative sequence of the mechanical motions of indicating torque at the mesial region of this tool will be better discussed in the following series of FIGS. 5–7.

Figure 5A:
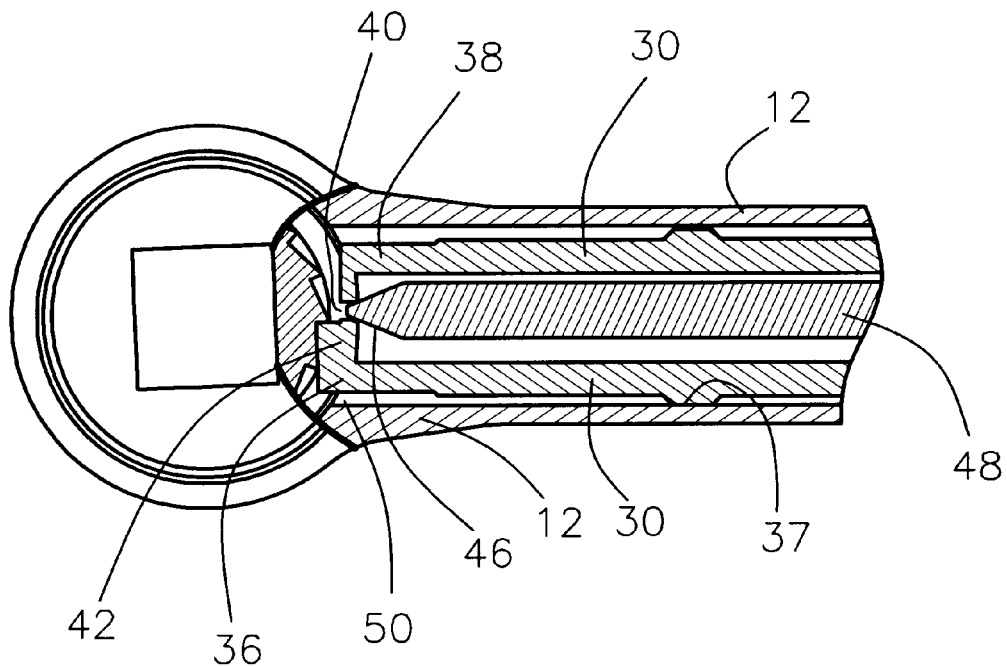
FIGS. 5A and 5B are distal and mesial views of the transducing and indicating mechanisms of the present invention, without any torque load.
Figure 5B:
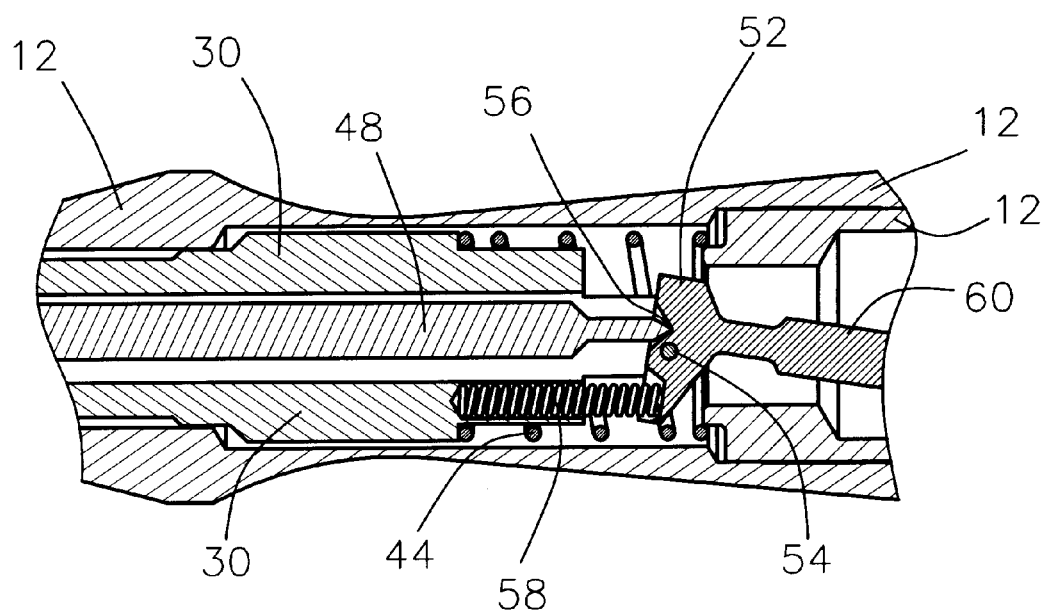

FIGS. 5A and 5B demonstrate the pre-load (no torque), relative positions of the mechanical elements for transduction and indication of torque. Transduction and indication occur respectively in the distal and mesial/proximal sections of the tool body 12. FIG. 5A illustrates the slidable pawl 30 and the sensing end 42 comprised of at least one flexing beam 36, and optionally a reference beam 38. As stated above, both beams 36, 38 are urged or biased towards the distal end of the tool body 12, by a compressed ratchet spring bearing against the proximal end of the pawl 30 and the tool body 12.

FIG. 5A further illustrates the flexing and reference beams 36, 38 having a gap 40 therebetween of minimal distance. Minimal distance is defined as the smallest possible distance between the two beams 36, 38 that would allow both beams 36, 38 to be substantially independent of the other beam's flexure.

As seen in FIG. 5A, there is little, if any, rotational engagement or deflection asserted against the cantilevered flexing beam 36 by the ratchet wheel 26 at this pre-load stage, because the torque wrench is not engaged to, or rotating any workpiece. Since there is no torque load asserted with this torque wrench, the ratchet wheel 26 is able to freely ratchet itself in the opposing, nonengaged, counterclockwise direction. Adjacent to the flexing beam 36 and on the opposite side of the gap 40, is sufficient clearance space 50 between the flexing beam 36 and the inside surface of the distal end of the tool body 12. This clearance space 50 allows a working range for deflection of the flexing beam 36, without impingement of the tool body 12.

FIG. 5A also shows the annular fulcrum 37 of the pawl 30 which is responsible for the cantilevering action of the flexing beam 36. Since the gap 40 is minimal in size, the wedge 46 of the rod 48 is only slightly inserted into the gap 40. This results in the furthest proximal position of the rod 48, as illustrated in FIG. 5B, as it directly bears upon and against the pivot bearing 56 of the pivot head 52. At this position, the pivot head 52 has rotated clockwise a few degrees around the axle 54 that secures it to the proximal end of the pawl 30. The compressed pivot spring 58, connected between the pawl 30 and the pivot head 52, is now compressed to the smallest position encountered by this mechanical indicating mechanism. This leaves the pointer 60, which is attached or integral to the pivot head 52, pointing to a torque value at the low end of the graduated scale located on the butt-end of the tool body.

FIG. 5B also illustrates the compressed ratchet spring 44 that bears against the proximal end of the pawl 30 and the tool body 12, thereby urging the pawl 30 towards the distal end of the tool body 12, where it engages the ratchet wheel.

Figure 6A:
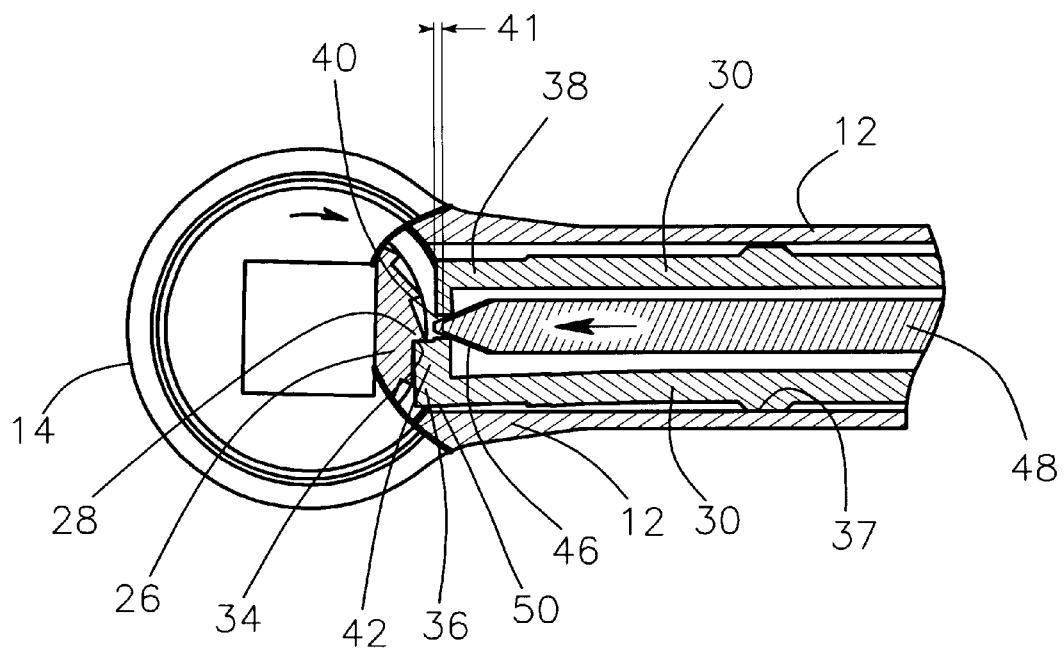
FIGS. 6A and 6B are distal and mesial views of the transducing and indicating mechanisms of the present invention, within a working-range torque load.
Figure 6B:
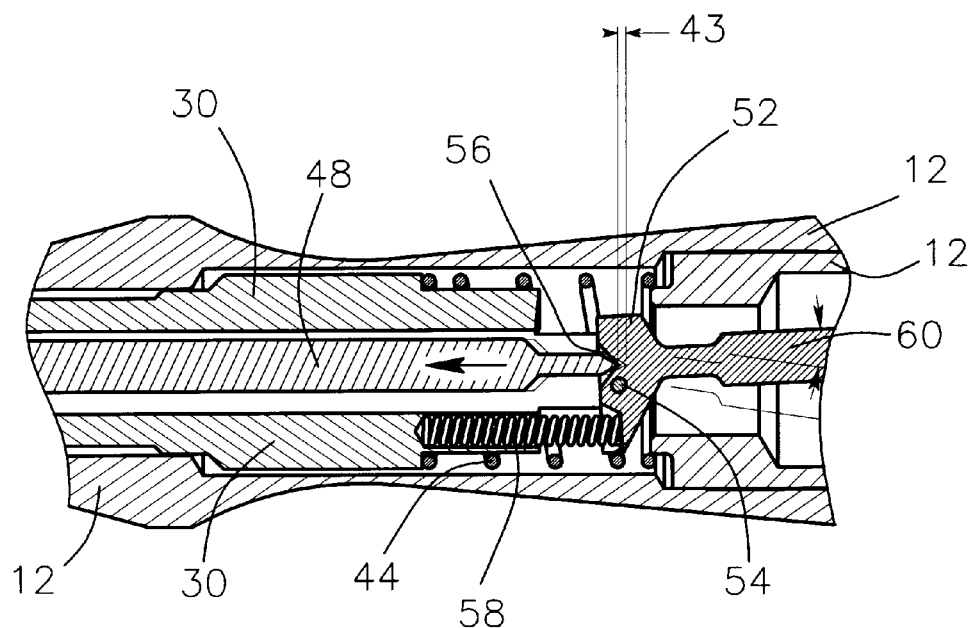

FIGS. 6A and 6B demonstrate the relative positions of the mechanical elements for transduction and indication of torque, as the ratchet wheel 26 is loaded with torque.

FIG. 6A illustrates the flexing and reference beams 36, 38 presently having a larger gap 40, than shown in FIG. 5A. The cantilevered flexing beam 36 has firmly engaged at least one of the ratchet teeth 28 with the protuberance 34 at the distal end of the flexing beam 36. This protuberance 34 is preferably shaped to complement the form of the ratchet teeth 28, which allows it to optimally engage any of the teeth 28. The resulting flexure of the flexing beam 36 causes the gap 40 to proportionally increase, and the wedge 46 end of the rod 48 to slide distally toward the ratchet wheel 26. Some clearance space 50 still remains between the flexing beam 36 and the inside surface of the tool body 12.

FIG. 6B shows the relative positions of the mechanical elements that result from the concurrent longitudinal sliding of the rod 48 away from the pivot bearing 56 of the pivot head 52, which allows the compressed pivot spring 58 to drive the counterclockwise rotation of the pivot head 52 by a few degrees. This rotation will cause deflection of the pointer 60 and allow some proportional value of torque to be indicated on the graduated scale.

It should be noted from FIG. 6A, that the reference beam 38 remains unflexed and stationary relative to the pawl 30 and the tool body 12. Since the function of the reference beam 38 is to remain stationary, those who are skilled in the art may design alternatives where the reference beam is integral to the tool body 12, rather than the pawl 30. Additionally, other indicating components such as an electronic proximity sensing element may eliminate the need for a reference beam 38 altogether.

Figure 7A:
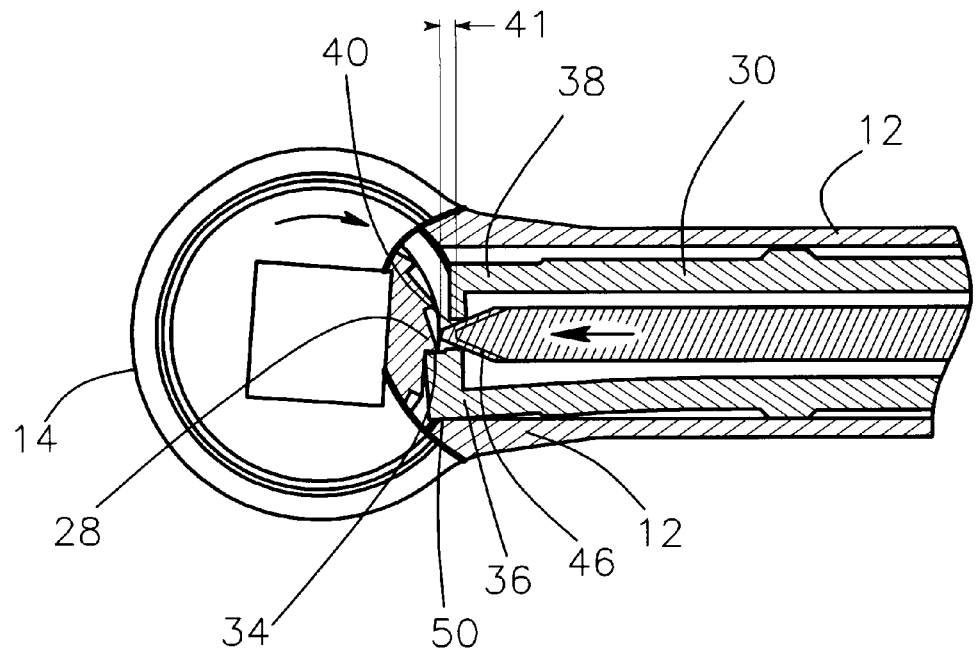
FIGS. 7A and 7B are distal and mesial views of the transducing and indicating mechanisms of the present invention, with an over-range torque load.
Figure 7B:
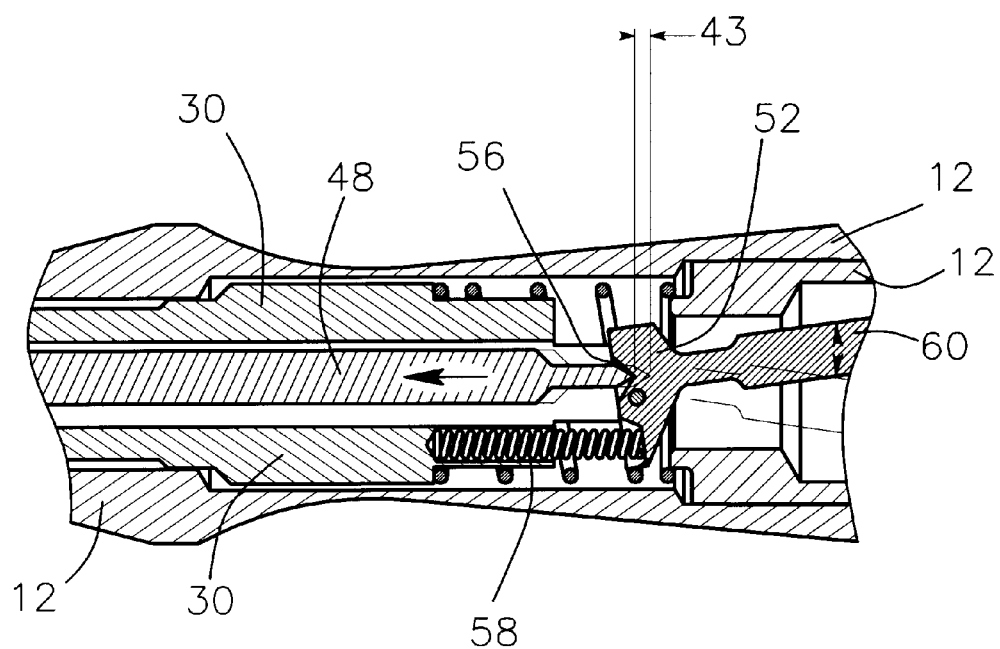

FIGS. 7A and 7B demonstrate the relative positions of the mechanical elements for transduction and indication of torque, as the ratchet wheel 26 is over-loaded with torque.

FIG. 7A illustrates the flexing and reference beams 36, 38 presently having an even largest gap 40 than in FIG. 5A or 6A. As in prior FIG. 6A, the cantilevered flexing beam 36 has firmly engaged at least one of the ratchet teeth 28 with the protuberance 34 at the distal end of the flexing beam 36. However, the resulting over-flexure of the flexing beam 36 that is induced in this case, causes the backside of the protuberance 34 to strike the distal, inside surface of the tool body 12. This impingement eliminates any of the clearance space that existed before torque over-load. The impingement also limits the torque over-load deflection of the flexing beam 36, thereby preventing any damage to the flexing beam 36 or transducing mechanism of the tool.

FIG. 7B, similar to FIG. 6B, shows the relative positions of the mechanical elements that result from the maximum displacement of the rod 48 away from the pivot bearing 56 of the pivot head 52. This over-range slide of the rod 48 allows the compressed pivot spring 58 to fully drive the counterclockwise rotation of the pivot head 52 by just a few more additional degrees. This rotation of the pivot head 52 will cause maximum deflection of the pointer 60 to an off-scale, out-of-range position on the graduated scale.

Figure 8:
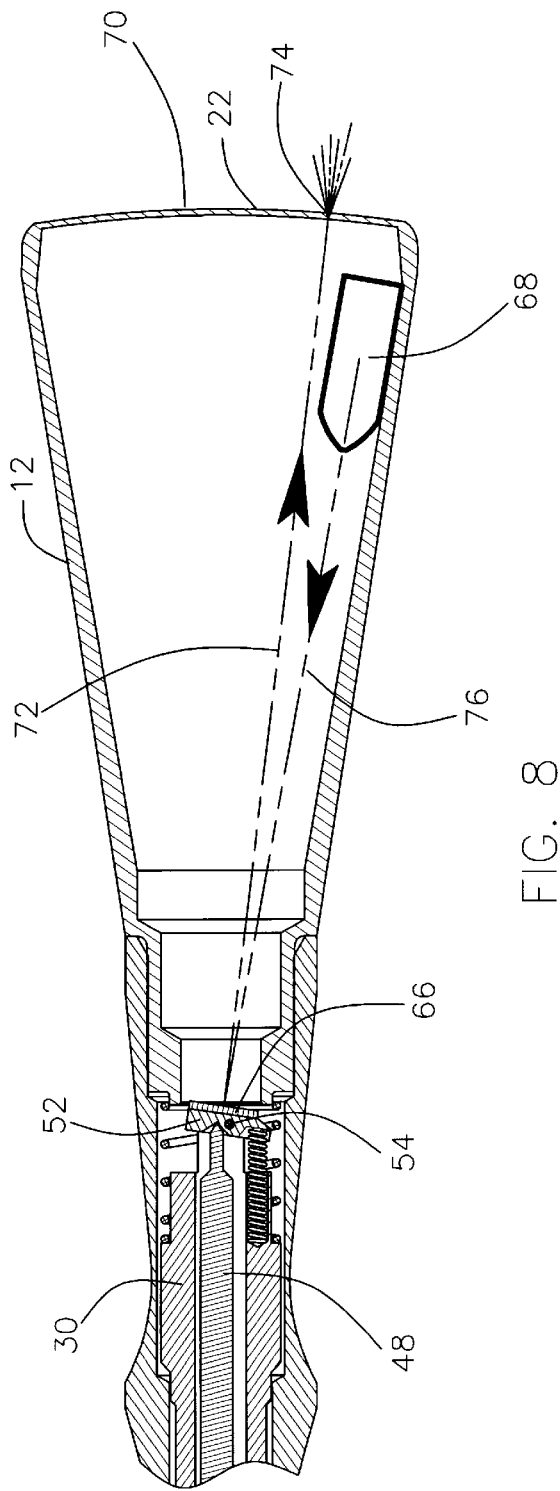
FIG. 8 is a cut-away view of an alternative embodiment utilizing optics for indicating torque.

FIG. 8 illustrates an alternative embodiment for indicating torque. Here the pivot head 52 has a mirror 66 or reflective surface facing the graduated scale 22. This mirror surface 66 pivots with the pivot head 52 around the axle 54, and reflects light 76 emitted from a light source 68. The light source 68 may be attached at the proximal end of the tool body 12. The graduated torque scale 22 has an adjacent translucent surface 70. A reflected light beam 72 strikes the translucent surface 70 thereby creating a lit spot 74 adjacent to the graduated scale 22.

Figure 9:
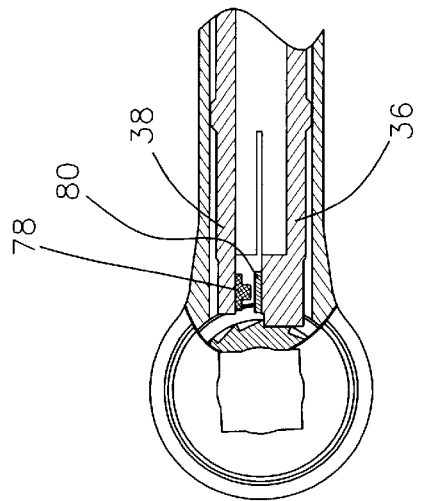
FIG. 9 is a cut-away view of an alternative embodiment utilizing electronics for transducing torque.

FIG. 9 shows an alternative embodiment for the indicating element, where a Hall effect sensor 78 is directly attached to the reference beam 38 opposite a magnet 80 attached to the flexing beam 36. These electronic components eliminated many sources of hysteresis and noise that resulted from the mechanical transduction and indication of torque. Similarly, other electronic components may be coupled to the flexing beam 36, so as to sense the deflection and produce or transmit a corresponding or proportional signal. Representative electronic components are characterized by a generic single or dual-element electronic detecting means, where one element is mounted on the reference beam or tool body, and the optional remaining element is installed on the torque sensing end of the pawl. The proximity of the deflecting sensing end is then sensed or detected and a proportional signal is then reported or transmitted to an indicating means. It is recognized by those skilled in the art, that in the case of dual-element systems, either element could be mounted on the sensor end of the pawl. Similarly, two-plate capacitance sensors; various types of strain gauges such as resistance strain gauges, electromagnetic strain gauges, variable capacitance strain gauges, and piezoelectric strain gauges; light emitting diodes (LEDs) and light detection sensors; proximity sensors; and other generic electrical sensors and detectors that are well know to those skilled in the art, may be used to transduce and/or indicate torque-induced deflection.

Figure 10:
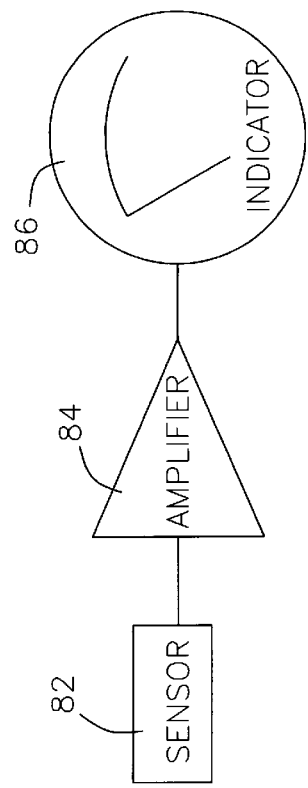
FIG. 10 is an electronic schematic diagram of a torque transducing sensor connected in series with an amplifier and a torque indicating meter.

FIG. 10 illustrates a representative electronic schematic whereby a generic electronic sensor 82 is serially connected to an amplifier 84 and output indicator 86.

A multi-step method for applying and indicating torque is comprised of providing a tool body having proximal and distal ends, where a ratchet wheel is disposed at the distal end of the tool body. Nested or form-fitted within the distal end of the tool body is the pawl that engages and ratchets the ratchet wheel using its torque sensing end. The opposing end of the pawl has a pivot head mounted transaxially to an end bracket. The sensor end of the pawl engages the ratchet wheel by interfacing with at least one of the ratchet teeth or by some other mechanism well known in the art. The ratchet teeth are located circumferentially around the ratchet wheel. The sensor end of the pawl is deflected by movement of the ratchet wheel as the tool body is manipulated against a workpiece. The deflection of the sensing end is transduced mechanically or electronically, and the resulting signal is then used to indicate torque values. Indicating torque may also be either mechanical or electronic, and the results are then displayed on the proximal end of the tool body.

Having described the preferred embodiment for the apparatus of the present invention, it will be apparent to one skilled in the art that other embodiments are also easily adapted by using the concepts discussed above. Accordingly, the invention should be limited only by the spirit and scope of the appended claims.

I claim:

1. A torque applying and indicating tool, comprising:
    a tool body having proximal and distal ends;
    a ratchet wheel disposed at said distal end of said tool body;
    a pawl nested within said distal end of said tool body and having a torque sensing end and an opposing end, said torque sensing end adapted to movably engage with and be deflected by said ratchet wheel; and
    a means for transducing deflection of said sensing end into a means for indicating torque.

2. The tool as recited in claim 1, wherein said torque sensing end of said pawl comprises a cantilevered flexing beam.

3. The tool as recited in claim 2, wherein said transducing means comprises a strain gauge coupled to said flexing beam, and adapted for measuring deflection of said flexing beam and transmitting a signal proportional to said measured deflection to said indicating means.

4. The tool as recited in claim 1, wherein said transducing means comprises:
    an electronic detecting means, having first and second elements;
    said first element disposed at said distal end of said tool body;
    said second element disposed on said torque sensing end of said pawl in proximity to said first element; and
    wherein said electronic detecting means is adapted to transmit a signal to said indicating means, said signal having a value proportional to the deflection of said torque sensing end.

5. The tool as recited in claim 1, wherein said transducing means comprises:
    a Hall effect sensor disposed at said distal end of said tool body;
    a magnet disposed on said torque sensing end of said pawl in proximity to said Hall effect sensor; and wherein said Hall effect sensor is adapted to transmit a signal to said indicating means, said signal having a value proportional to the deflection of said torque sensing end.

6. The tool as recited in claim 1, wherein said transducing means comprises:

a magnet disposed at said distal end of said tool body;

a Hall effect sensor disposed on said torque sensing end of said pawl in proximity to said magnet; and wherein said Hall effect sensor is adapted to transmit a signal to said indicating means, said signal having a value proportional to the deflection of said torque sensing end.

7. The tool as recited in claim 1, wherein said transducing means comprises:

a capacitive sensor having first and second capacitance plates;

said first capacitance plate disposed at said distal end of said tool body;

said second capacitance plate disposed on said torque sensing end of said pawl; and wherein said capacitive sensor is adapted to transmit a signal to said indicating means, said signal proportional to the deflection of said torque sensing end.

8. The tool as recited in claim 7, wherein said second capacitance plate is said pawl.

9. The tool as recited in claim 1, wherein said sensing end of said pawl further comprises a reference beam juxtaposed said flexing beam, said flexing beam adapted to be movable relative to said reference beam, said beams having a gap interposed therebetween.

10. The tool as recited in claim 9, wherein said transducing means comprises:

a rod positioned adjacent to said pawl, said rod having opposing first and second ends, said first end is tapered and slidably wedged between said gap, said rod movable with respect to said pawl upon deflection of said flexing beam; and said second end of said rod connected to said indicating means.

11. The tool as recited in claim 10, wherein said indicating means comprises:

a pointer having distal and proximal ends;

a pivot head connected to said distal end of said pointer, said pivot head mounted to said opposing end of said pawl, said pivot head coupled to said second end of said rod; and a spring interposed between said pawl and said pivot head, and adapted for driving the deflection of said pointer.

12. The tool as recited in claim 10, wherein said indicating means comprises:

a mirror movably mounted to said opposing end of said pawl, and said mirror coupled to said second end of said rod;

a light emitting means located at said proximal end of said tool body, and adapted to project light onto said mirror; and a spring interposed between said pawl and said mirror, and adapted to drive the movement of said mirror.

13. The tool as recited in claim 1, further comprising a springable means secured to said tool body for urging said sensing end towards said ratchet wheel.

14. The tool as recited in claim 1, wherein said proximal end of said tool body has a graduated scale located thereon.

15. A torque indicating ratchet wrench, comprising:

a tool body having proximal and distal ends;

a ratchet wheel disposed at said distal end of said tool body;

a pawl fitted within said distal end of said body and having a torque sensing end and an opposing end;

said pawl having a fulcrum from which said torque sensing end projects toward said ratchet wheel;

said torque sensing end adapted for movable engagement with and deflected by said ratchet wheel; and a means for transmitting deflection of said torque sensing end to a means for indicating torque.

16. The ratchet wrench as recited in claim 15, wherein said torque sensing end comprises:

a flexing beam; and a reference beam positioned adjacent said flexing beam, said beams having a gap therebetween.

17. The ratchet wrench as recited in claim 16, wherein said transmitting means comprises:

a rod positioned parallel to said pawl and having distal and proximal ends, said distal end tapered and movably disposed between said beams; and said proximal end of said rod coupled to said indicating means.

18. The ratchet wrench as recited in claim 17, wherein said indicating means comprises:

a pivot head mounted to said opposing end of said pawl, said pivot head adapted to interface with said proximal end of said rod;

a pointer connected to said pivot head and projecting toward said proximal end of said tool body; and a rotational bias means disposed between said pawl and said pivot head, said bias means adapted for driving the rotation of said pivot head.

19. The ratchet wrench as recited in claim 18, wherein said rotational bias means is a spring.

20. A method for applying and indicating torque, comprising:

providing a tool body having proximal and distal ends;

disposing a ratchet wheel at the distal end of the tool body;

nesting a pawl within the distal end of the tool body, the pawl having a torque sensing end and an opposing end;

engaging the sensing end of the pawl to the ratchet wheel;

deflecting the sensing end of the pawl upon movement of said ratchet wheel with respect to the tool body; and transducing the deflection of the sensing end and indicating torque value based thereon.

* * * * *